United States Patent [19]

Venkatesan et al.

[11] Patent Number: 5,294,617
[45] Date of Patent: Mar. 15, 1994

[54] ANGIOTENSIN II RECEPTOR BLOCKING 2,3,6 SUBSTITUTED QUINAZOLINONES

[75] Inventors: Aranapakam M. Venkatesan, Elmhurst; Jeremy I, Levin, Nanuet, both of N.Y.

[73] Assignee: American Cyanamid Company, Wayne, N.J.

[21] Appl. No.: 52,932

[22] Filed: Apr. 23, 1993

[51] Int. Cl.$^5$ ............... A61K 31/505; C07D 239/90; C07D 239/91
[52] U.S. Cl. ........................ 514/259; 514/260; 544/284; 544/287
[58] Field of Search ............ 514/259, 260; 544/284, 544/287

[56] References Cited

U.S. PATENT DOCUMENTS 5,202,322   4/1993   Allen et al. ................. 514/228.2

*Primary Examiner*—Mukund J. Shah
*Assistant Examiner*—Matthew Y. Grumbling
*Attorney, Agent, or Firm*—T. S. Szatkowski

[57] ABSTRACT

This disclosure describes novel 2, 3, 6 substituted quinazolinones having the formula

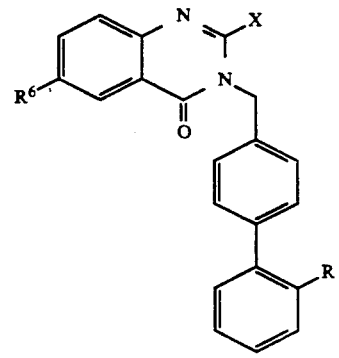

wherein $R^6$, X and R are defined in the specification which have activity as angiotensin II (AII) antagonists.

21 Claims, No Drawings

ANGIOTENSIN II RECEPTOR BLOCKING 2,3,6 SUBSTITUTED QUINAZOLINONES

FIELD OF THE INVENTION

This invention relates to certain novel 2,3,6 substituted quinazolinone compounds which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which have angiotensin II-antagonizing properties and are useful as antihypertensives:

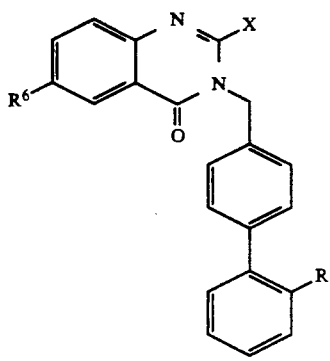

wherein
R is

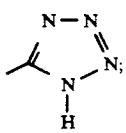

X is straight or branched chain lower alkyl of 3 to 5 carbon atoms;
$R^6$ is

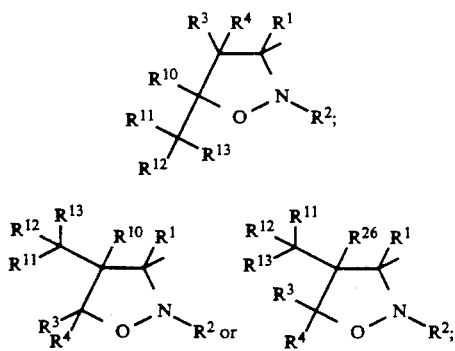

$R^1$ is H, straight chain lower alkyl of 1 to 4 atoms, —$CF_3$, —CN,

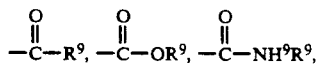

phenyl, substituted phenyl (substitution selected from mono-lower alkyl of 1 to 3 carbon atoms, —$CF_3$, nitro, O-alkyl of 1 to 3 carbon atoms), pyridine, thiophene or furan;

$R^2$ is straight or branched chain lower alkyl of 1 to 4 carbon atoms, cycloalkyl (rings of 3 to 8 carbon atoms), phenyl, substituted phenyl (substitution selected from mono-lower alkyl of 1 to 3 carbon atoms), —$CF_3$, nitro, O-alkyl of 1 to 3 carbon atoms), pyridine, thiophene, furan, benzyl, substituted benzyl (substitution selected from mono-lower alkyl of 1 to 3 carbon atoms, —$CF_3$, nitro, O-alkyl of 1 to 3 carbon atoms);

$R^3$ is H, straight or branched lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms), pyridine, thiophene, furan, —CHO, —$CO_2R^{19}$ or

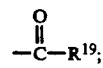

$R^4$ is H, straight or branched chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms), pyridine, thiophene, furan, —CHO, —$OR^{19}$, —$CO_2R^{19}$ or

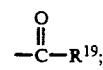

$R^9$ is hydrogen, straight or branched chain lower alkyl of 1 to 4 carbon atoms;

$R^{10}$ is H, straight or branched chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms), pyridine, thiophene, or furan;

$R^{11}$ is H, straight or branched chain lower alkyl of 1 to 4 carbon atoms, —$CF_3$, phenyl, substituted phenyl (substitution selected from mono-lower alkyl of 1 to 3 carbon atoms, —$CF_3$, nitro, O-alkyl of 1 to 3 carbon atoms), pyridine, thiophene, furan, benzyl, substituted benzyl (substitution selected from mono-lower alkyl of 1 to 3 carbon atoms, —$CF_3$, nitro, O-alkyl of 1 to 3 carbon atoms), —$OR^9$, O-phenyl, O-substituted phenyl (substitution selected form mono-lower alkyl of 1 to 3 carbon atoms, —$CF_3$, nitro, O-alkyl of 1 to 3 carbon atoms), O-pyridine, O-thiophene, O-furan, —$NH_2$, —$NHR^{19}$, —$NR^{19}R^{19}$, —$CO_2R^{19}$, or —$CONR^9R^9$;

$R^{12}$ is H, straight or branched chain lower alkyl of 1 to 4 carbon atoms, —$CF_3$, phenyl, substituted phenyl (substitution selected from mono-lower alkyl of 1 to 3 carbon atoms, —$CF_3$, nitro, O-alkyl of 1 to 3 carbon atoms), pyridine, thiophene, furan, benzyl, substituted benzyl (substitution selected from mono-lower alkyl of 1 to 3 carbon atoms, —$CF_3$, nitro, O-alkyl of 1 to 3 carbon atoms), —$OR^9$, O-phenyl, O-substituted phenyl (substitution selected from mono-lower alkyl of 1 to 3 carbon atoms, —$CF_3$, nitro, O-alkyl of 1 to 3 carbon atoms), O-pyridine, O-thiophene, O-furan, —$NH_2$, —$NHR^{19}$, —$NR^{19}R^{19}$, —$CO_2R^{19}$, or —$CONR^9R^9$;

$R^{13}$ is H, straight or branched chain lower alkyl of 1 to 4 carbon atoms, —$CF_3$, phenyl, substituted phenyl (substitution selected from mono-lower alkyl of 1 to 3 carbon atoms, —CF$_3$, nitro, O-alkyl of 1 to 3 carbon atoms) pyridine, thiophene, furan, benzyl, substituted benzyl (substitution selected from mono-lower alkyl of 1 to 3 carbon atoms, —CF$_3$, nitro, O-alkyl of 1 to 3 carbon atoms) —OR$^9$, O-phenyl, O-substituted phenyl(substitution selected from mono-lower alkyl of 1 to 3 carbon atoms, —CF$_3$, nitro, O-alkyl of 1 to 3 carbon atoms), O-pyridine, O-thiophene, O-furan, —NH$_2$, —NHR$^{19}$, —NR$^{19}$R$^{19}$, —CO$_2$R$^{19}$, or —CONR$^9$R$^9$;

R$^{19}$ is straight or branched chain lower alkyl of 1 to 4 carbon atoms;

R$^{26}$ is —CHO, —OR$^{19}$, —CO$_2$R$^{19}$ or

and pharmaceutically acceptable salts of these compounds.

The present invention also provides novel intermediate compounds, methods for making the novel 2, 3, 6 substituted quinazolinone angiotensin II antagonizing compounds, methods for using the novel quinazolinone angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

Referring to Scheme I, the corresponding anthranilic acid 2, where R$^5$ is I, Br or CH$_3$, are heated to reflux in alkyl acid anhydride 3 wherein X is alkyl of 3 to 5 carbon atoms to provide the 4 H-3,1-benzoxain-4-ones 4 which are isolated by concentrating the reaction mixtures and used without further purification. When the 4H-3,1-benzoxazin-4-ones 4 are refluxed in ethyl alcohol containing ammonia, or ammonium hydroxide solution, the quinazolinone intermediates 5 are obtained.

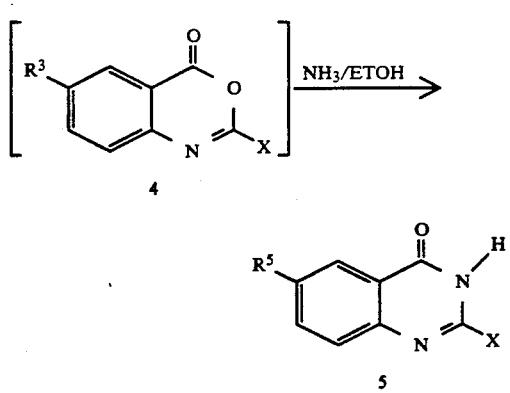

The quinazolinone intermediates 5 are modified according to the following reaction schemes to obtain the novel quinazolinone angiotensin II antagonizing compounds of the present invention.

In Scheme II, 6-methylquinazolinone 6, as prepared by Scheme I, is brominated with N-bromosuccinimide to give the bromomethyl compound 7. Hydrolysis of the bromide with aqueous potassium carbonate in dimethylsulfoxide yields the primary alcohol 8. The alcohol 8 is oxidized with pyridinium dichromate in N,N-dimethylformamide to afford aldehyde 9. The aldehyde 9 is reacted with a variety of Grignard Reagents R$^1$MgBr or lithium reagents R$^1$Li in tetrahydrofuran where R$^1$ is hereinbefore defined, with the proviso that for this scheme R$^1$ cannot be H, $$-\overset{O}{\underset{\|}{C}}-R^9, \quad -\overset{O}{\underset{\|}{C}}-OR^9, \text{ or } -\overset{O}{\underset{\|}{C}}-NR^9R^9$$

to give the desired secondary alcohol 10. Alcohol 10 is oxidized with pyridinium dichromate in N,N-dimethylformamide to afford ketone 11.

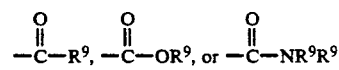

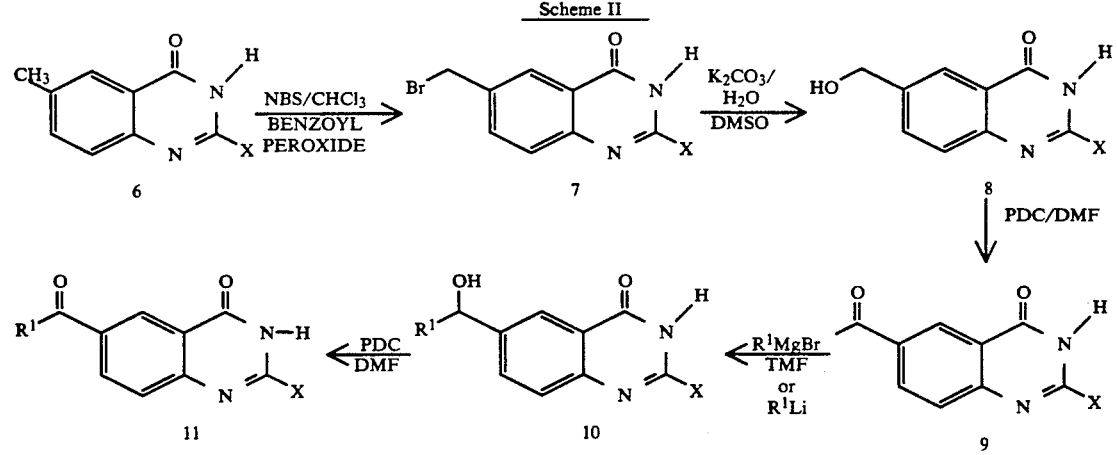

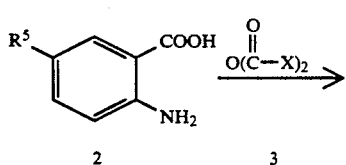

In an alternate route to 9, as shown in Scheme III, 2-alkyl substituted-6-iodo-4(1H) quinazolinone 12 is reacted via a palladium catalyzed carbonylation to give aldehyde 9. Additionally, 12 is converted to ester 13 by palladium (II) catalyzed coupling in the presence of carbon monoxide and methanol. Reduction of 13 with lithium aluminum hydride in tetrahydrofuran gives alcohol 8. Alcohol 8 is oxidized with pyridinium dichromate to yield aldehyde 9.

tion of 17 with catalytic mercuric sulfate-sulfuric acid in acetic acid gives ketone 18.

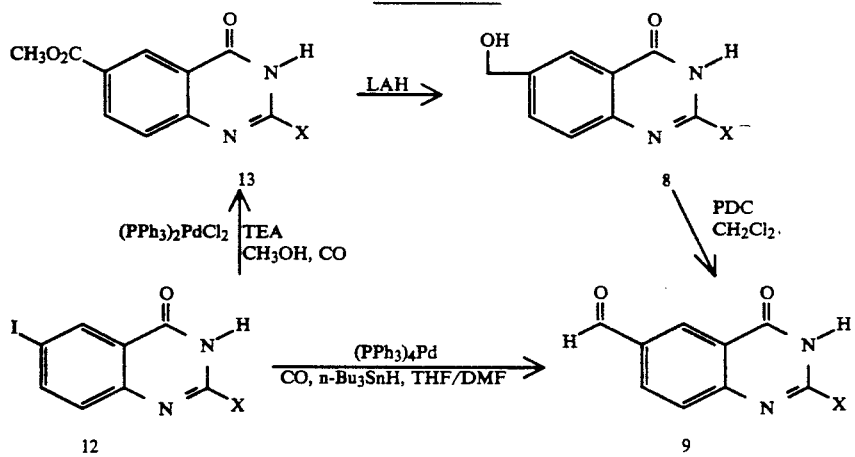

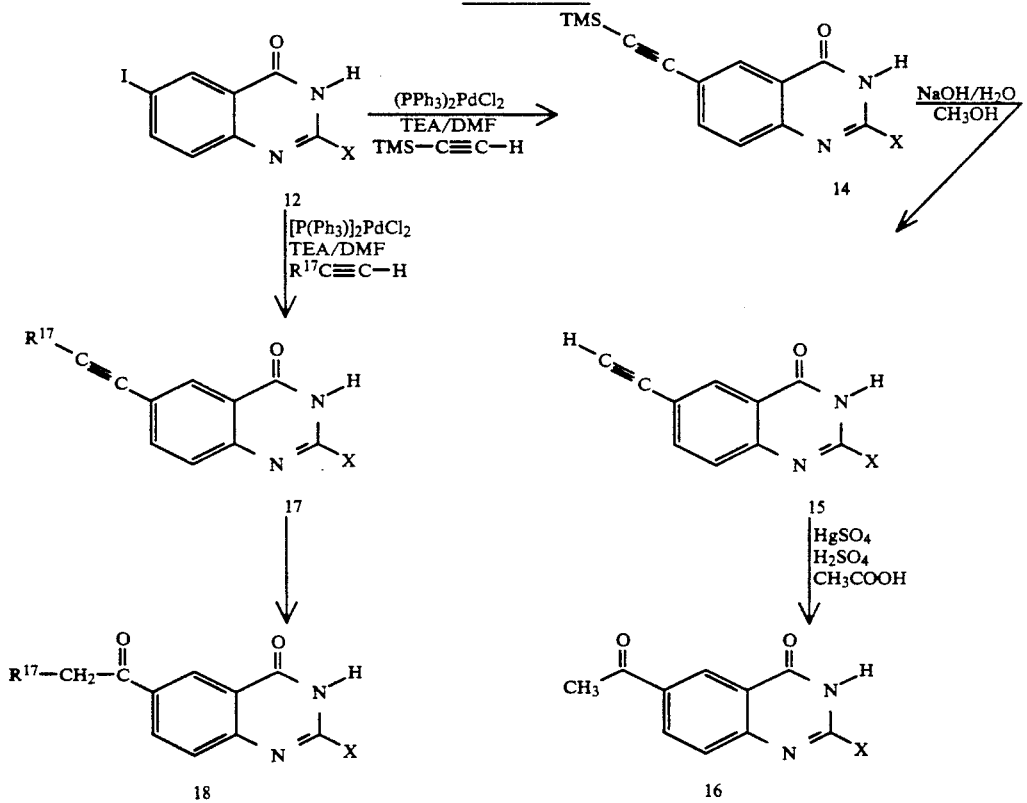

As shown in Scheme IV, the palladium (II) catalyzed coupling of (trimethylsilyl)acetylene with 2-alkylsubstituted-6-iodo-4(1H)-quinazolinone 12 yields the acetylenic quinazolinone 14. Desilylation of the acetylene with sodium hydroxide in water-methanol gives the terminal acetylene 15. Hydration of acetylene 15 with catalytic mercuric sulfate-sulfuric acid in acetic acid affords methyl ketone 16. The palladium (II) catalyzed coupling of substituted acetylenes where $R^{17}$ is defined as straight or branched lower alkyl of 1 to 4 carbon atoms with 2-alkylsubstituted-6-iodo-4(1H)-quinazolinone 12 yields the acetylenic quinazolinone 17. Hydra- As shown in Scheme V, aldehyde or ketone 11, wherein $R^1$ and X are hereinbefore defined, is reacted with N-substituted hydroxylamine 19, wherein $R^2$ is hereinbefore defined, at room temperature in ethanol to give the quinazolinone $N^6$-oxide 20.

Scheme V

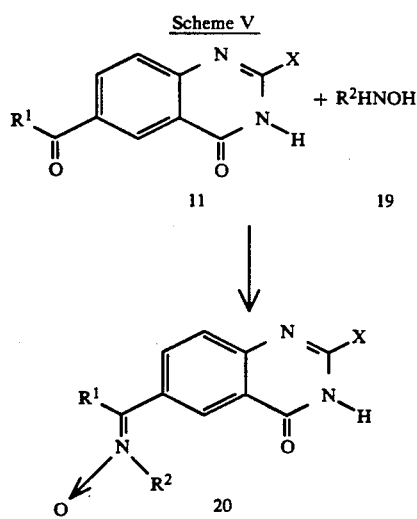

Scheme VI

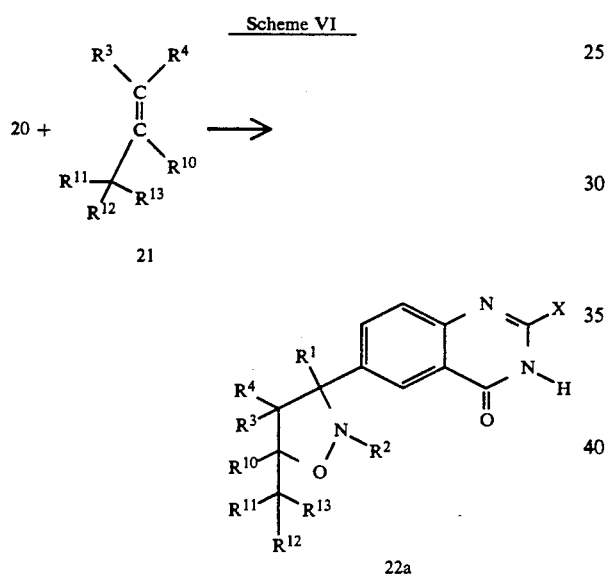

-continued
Scheme VI

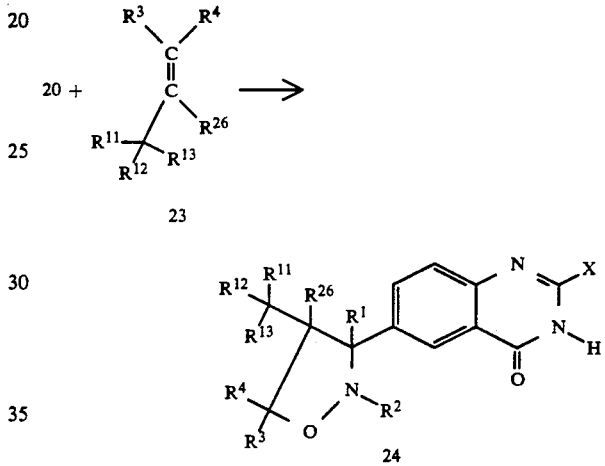

As shown in Scheme VI, quinazolinone N⁶-oxide 20 is heated with olefin 21 in xylene at reflux, wherein $R^3$, $R^4$, $R^{10}$, $R^{11}$, $R^{12}$ and $R^{13}$ are hereinbefore defined to give 3-isoxazolidinyl-4(1H)-quinazolinone 22a and 22b.

Scheme VII

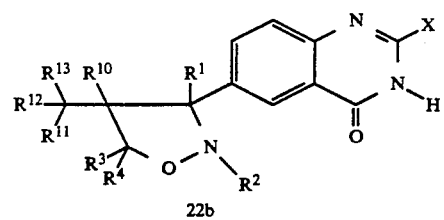

As shown in Scheme VII, quinazolinone N⁶-oxide 20 is heated with olefin 23 in xylene wherein $R^3$, $R^4$, $R^{11}$, $R^{12}$, $R^{13}$ and $R^{26}$ are hereinbefore defined, to give 24.

Scheme VIII

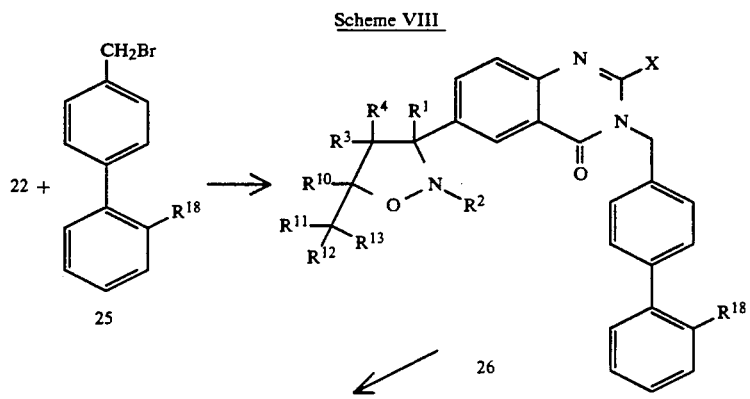

Scheme VIII

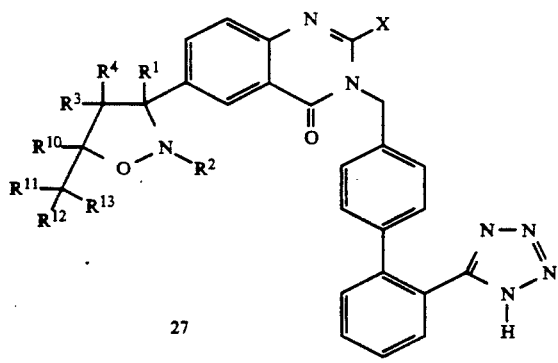

As described in EP O 497 150, biphenyl 25 is attached to quinazolinone intermediate 22a or 22b by initially alkylating the quinazolinone with a para-substituted benzyl bromide and subsequently attaching a second phenyl moiety containing a trityl protected tetrazole or a cyano via a transition metal catalyzed coupling at the para position of the first phenyl ring. Alternatively, the coupling of quinazolinone intermediate 22a where $R^1, R^2, R^3, R^4, R^{10}, R^{11}, R^{12}, R^{13}$ and X are hereinbefore defined with biphenyl 25 where $R^{18}$ is a trityl protected tetrazole prepared by the methods of N. B. Mantlo et. al., *J. Med. Chem.* 34, 2919-2923 (1991) or cyano prepared by the methods outlined in D. J. Carini, *J. Med. Chem.* 34, 2525-2547 (1991) is illustrated in Scheme VIII and gives coupled product 26 by dissolving 22 and 25 in acetone or another suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium hexamethyl- disilazide for 2–48 hours, at 20°-60° C. The obtained alkylated quinazolinone 26 may be purified by chromatography or used as is in further transformations and/or deprotection. Reaction of 26 where $R^{18}$ is cyano with sodium azide in the presence of tri-n-butyltin chloride in refluxing xylene affords the desired tetrazole 27. Contemplated equivalents to tri-n-butyltin chloride include tri-(lower alkyl $C_1$-$C_4$)tin chlorides and bromides. Comtemplated equivalents to sodium azide include potassium azide, lithium azide and cesium azide. Hydrolysis of 26 where $R^{18}$ is a trityl protected tetrazole with methanol-tetrahydrofuran at room temperature to reflux or a catalytic amount of hydrochloric acid or other suitable acid such as sulfuric, trifluoroacetic or hydrogen chloride for 10 minutes to 24 hours at room temperature affords the free tetrazole 27. Quinazolinone intermediate 22b may be similarly coupled to 25.

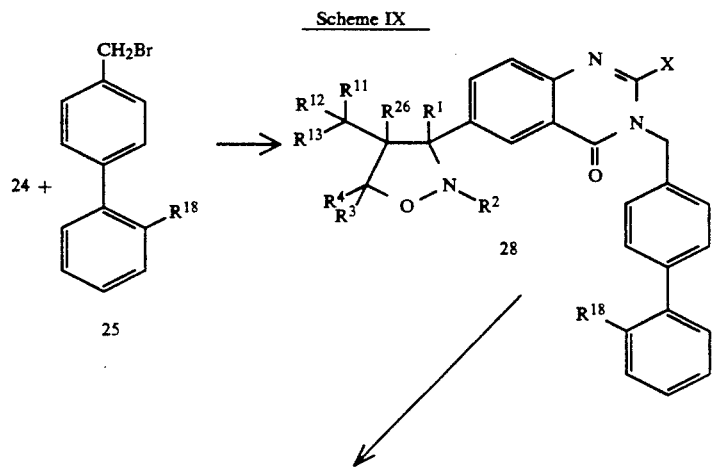

Scheme IX

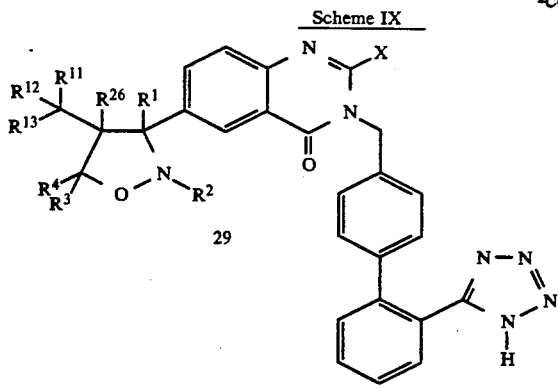

29

As described in EP O 497 150, biphenyl 25 is attached to quinazolinone intermediate 24 by initially alkylating the quinazolinone with a para-substituted benzyl bromide and subsequently attaching a second phenyl moiety containing a trityl protected tetrazole or a cyano via a transition metal catalyzed coupling at the para position of the first phenyl ring. Alternatively, the coupling of quinazolinone intermediate 24 where $R_1, R^2, R^3, R^4, R_{11}, R^{12}, R^{13}, R^{26}$ and X are hereinbefore defined with biphenyl 25 where $R^{18}$ is a trityl protected tetrazole prepared by the methods of N. B. Mantlo et. al., *J. Med. Chem* 34 2919-2923 (1991) or cyano prepared by the methods outlined in D. J. Carini, *J. Med. Chem.* 34, 2525-2547 (1991) is illustrated in Scheme IX and gives coupled product 28 by dissolving 24 and 25 in acetone or another suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium hexamethyldisilazide for 2-48 hours, at 20°-60° C. The obtained alkylated quinazolinone 28 may be purified by chromatography or used as is in further transformations and/or deprotection. Reaction of 28 where $R^{18}$ is cyano with sodium azide in the presence of tri-n-butyltin chloride in refluxing xylene affords, the desired tetrazole 29. Contemplated equivalents to tri-n-butyltin chloride include tri-(loweralkyl $C_1-C_4$) tin chlorides and bromides. Contemplated equivalents to sodium azide include potassium azide, lithium azide and cesium azide. Hydrolysis of 28 where $R^{18}$ is a trityl protected tetrazole with methanol-tetrahydrofuran at room temperature to reflux or a catalytic amount of hydrochloride acid or other suitable acid such as sulfuric, trifluoroacetic or hydrogen chloride for 10 minutes to 24 hours at room temperature affords the free tetrazole 29.

Reactions are performed in a solvent appropriate to the reagents and materials employed and suitable for the transformation being effect. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium magnesium and ammonium salts.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation are illustrated by the following non-limiting examples.

Example 1

2-Butyl-6-(methyl)-4(1H)-quinazolinone

To 20.0 g of 2-amino-5-methylbenzoic acid is added 60 ml of valeric anhydride. The mixture is heated at reflux for 18 hours and then concentrated under reduced pressure. The resulting brown solid residue is dissolved in a mixture of 200 ml of 30% of ammonium hydroxide solution and 300 ml of ethyl alcohol. This mixture is heated at reflux for 5 hours and then allowed to cool to room temperature. After cooling, the precipitate is collected by filtration. The cake is washed with ethanol and water, then dried under vacuum to give 8.92 g of the quinazolinone as a white solid. CI MASS SPEC MH+ =217.

Example 2

2-Butyl-6-iodo-4(1H)-quinazolinone

The method of Example 1 is used with 2-amino-5-iodobenzoic acid to prepare the desired product, m.p. 257°-258° C.

Example 3

2-Butyl-6-(bromomethyl)-4(1H)-quinazolinone

To a suspension of 3.50 g of 6-methylquinazolone in 100 ml of chloroform is added 3.39 g of N-bromosuccinimide and 0.25 g of benzoyl peroxide. The reaction mixture is heated at reflux for 18 hours and then filtered hot. A precipitate of 2.21 g of an in separable mixture of the desired bromide and starting 6-methyl-quinazolinone is obtained and used in Example 4 without further purification.

Example 4

2-Butyl-6-(hydroxymethyl)-4(1H)-quinazolinone

To a suspension of 2.0 g of impure 2-butyl-6-(bromomethyl)-4(1H)-quinazolinone (Example 3) in 35 ml of dimethylsulfoxide and 20 ml of water is added 1.0 g of potassium carbonate. The reaction mixture is heated at reflux for 6 hours, resulting in a complete solution. Upon cooling slowly to room temperature a white precipitate forms and is collected by filtration. The filter cake is purified by flash chromatography on silical gel, eluting with 9:1 chloroform-methanol to give 0.67 g of the desired product as a white solid. CI MASS SPEC 233 (M+H).

Example 5

2-Butyl-1,4-dihydro-4-oxo-6-quinazolinecarboxaldehyde

To a solution of 0.3 g of 2-butyl-6-(hydroxymethyl)-4(1H)-quinazolinone in 3.5 ml of dry N,N-dimethylformamide is added 1.7 g of pyridinium dichromate. The reaction mixture is stirred at room temperature for 16 hours and then poured into 125 ml of water. The resulting precipitate is removed by filtration and the filtrate extracted with 9:1 chloroform-methanol. The combined organic extracts are dried over magnesium sulfate, filtered and concentrated in vacuo and combined with the precipitate above. The combined solids are purified by flash chromatography on silica gel by eluting with 1:1 ethyl acetate-hexanes to give 0.27 g of the desired product. CI MASS SPEC 231(M+H).

Example 6

2-butyl-1,4-dihydro-4-oxo-6-quinazolinecarboxaldehyde

To a solution of 1.0 g of 2-butyl-6-iodo-4-(1H)-quinazolinone and 0.355 g of tetrakis(triphenylphosphine)palladium in 15 ml of tetrahydrofuran and 5 ml of N,N-dimethylformamide, heated to 55° C. under an atmosphere of carbon monoxide is added a solution of 1.40 g of tri-n-butyltin hydride in 2.5 ml of toluene over 6 hours via a syringe pump. After the addition is complete the reaction is allowed to cool to room temperature, diluted with brine and extracted with chloroform. The combined organics are concentrated in vacuo and the resulting residue triturated with ether. The precipitate is collected by filtration and purified by flash chromatography on silica gel, eluting with 1:1 ethyl acetate-hexanes to give 0.35 g of the desired product, m.p. 242°-244° C.

Example 7

2-Butyl-6-[(trimethylsilyl)ethylnyl]-4(1H)-quinazolinone

To a solution of 1.0 g of 2-butyl-6-iodo-4(1H)-quinazolinone 0.043 g of bis(triphenylphosphine)palladium (II) chloride and 5.8 mg of copper (I) iodide in 5.0 ml of N,N-dimethylformamide and 5.0 ml of triethylamine is added 0.36 g of (trimethylsilyl) acetylene. The resulting reaction mixture is heated at 45° C. for 1 hour and then 65° C. for 5 hours. Upon cooling, the reaction mixture is concentrated in vacuo and the residue purified by flash chromatography on silica gel, eluting with 1:3 ethyl acetate-hexane to yield 0.75 g of the desired product as a white solid. CI MASS SPEC 299(MH+).

Example 8

2-Butyl-6-ethylnyl-4(1H)-quinazolinone

To a solution of 0.70 g of 2-butyl-6-[(trimethylsilyl)ethynyl]-4(1H)-quinazolinone in 20 ml of methanol and 20 ml of tetrahydrofuran is added 10.0 ml of 1.0 N sodium hydroxide solution. The reaction is stirred at room temperature for 2 hours and then diluted with 5% hydrochloric acid solution until the pH is 2. The resulting tan precipitate is collected by filtration and dried in vacuo to yield 0.50 g of the desired product.
CI MASS SPEC 227(MH+).

Example 9

6-Acetyl-2-butyl-4(1H)-quinazolinone

To a solution of 1.20 g of 2-butyl-6-ethynyl-4(1H)-quinazolinone in 90 ml of acetic acid is added 0.45 g of mercuric sulfate, 0.9 ml of water and 0.3 ml of sulfuric acid. The reaction mixture is heated at reflux for 5 hours, cooled to room temperature and quenched with with 150 ml of water. The resulting mixture is concentrated in vacuo, diluted with 150 ml of water and extracted with 6:1 chloroform-methanol. The combined organics are dried over magnesium sulfate, filtered and concentrated in vacuo. The residue is purified by flash chromatography on silica gel, eluting with 1:1 ethyl acetate-hexanes to give 0.67 g of the desired product as a white solid.
CI MASS SPEC 245(MH+).

Example 10

2-Butyl-6-[(methylimino]-4(1H)-quinazolinone N6-oxide

To a stirred slurry of 4.1 g of N-methylhydroxylamine hydrochloride in 50 ml of 0° C. absolute ethanol is added 2.2 g of sodium methoxide. The reaction mixture is stirred for 15 minutes and 2.3 g of 2-butyl-1,4-dihydro-4-oxo-6-quinazoline-carboxaldehyde added. The reaction mixture is stirred at room temperature for 2 hours, then poured into water. The resulting crystals are collected by filtration, washed well with water and air dried to afford 2.3 g of the desired product, m.p. 206° C.

Example 11

TRANS-2-butyl-6[5-(hydroxymethyl)-2-methyl-3-isoxazolidinyl]-4(1H)-quinazolinone

Example 12

CIS-2-butyl-6-5-(hydroxymethyl)-2-methyl-3-isoxazolidinyl]-4(1H)-quinazolinone

A mixture of 450 mg of 2-butyl-6-[(methylimino)methyl]-4(1H)-quinazolinone N6-oxide and 2 ml of allyl alcohol in 10 ml of toluene is refluxed under inert gas for 48 hours. The volatiles are concentrated in vacuo and the residue is purified by chromatography on silica gel using from 50–90% ethyl acetate in hexanes. The faster moving trans isomer totals 200 mg, m.p. 130° C. and the slower moving cis isomer totals 280 mg, m.p. 125° C.

Example 13

CIS-2-butyl-6-[5-(hydroxymethyl)-2-methyl-3-isoxazolidinyl]-3-[[2'-[1-(triphenylmethyl)-1H-tetrazol-5-yl][1,1'-biphenyl]-4-yl]methyl]-4(3H)-quinazolinone A mixture of 200 mg of CIS-2-butyl-6-[5-(hydroxymethyl)-2-methyl-3-isoxazolidinyl]-4(1H)-quinazolinone, 550 mg of 5-(4,-(bromomethyl)-[1,1'-biphenyl]-2-yl]-1-(triphenylmethyl)-1H-tetrazole and 2 g of potassium carbonate is refluxed in 100 ml of acetone for 24 hours. The reaction mixture is filtered and washed well with acetone. The combined filtrates are evaporated in vacuo to afford a residue which is purified by chromatography on silica gel using 1:1 ethyl acetate-hexanes up to 3:1 ethyl acetate:hexanes to give 200 mg of the desired product. FAB MASS SPEC LOW RESOLUTION 795(M+1)

Example 14

TRANS-2-butyl-6-[5-(hydroxymethyl)-2-methyl-3-isoxazolidinyl]-3-[[2'-[1-(triphenylmethyl)-1H-tetrazol-5-yl][1,1'-biphenyl]-4-yl]methyl]-4(3H)-quinazolinone A mixture of 220 mg of TRANS-2-butyl-6-[5-(hydroxymethyl)-2-methyl-3-isoxazolidinyl]-4(1H)-quinazolinone, 552 mg of 5-(4,-(bromomethyl)-[1,1'-biphenyl]-2-yl]-1-(triphenylmethyl)-1H-tetrazole and 2 g of potassium carbonate is refluxed in 100 ml of acetone for 24 hours. The reaction mixture is filtered and washed well with acetone. The combined filtrates are evaporated in vacuo and the residue purified by chromatography on silica gel using 1:1 ethyl acetate-hexanes to afford 350 mg of the desired product as a spongy solid. FAB MASS SPEC LOW RESOLUTION 795(m+1)

Example 15

CIS-2-butyl-6-5-(hydroxymethyl)-2-methyl-3-isoxazolidinyl]-3-[[2'-(1H-tetrazol-5[1,1'-biphenyl]-4-yl]methyl]-4(3H)-quinazolinone A mixture of 200 mg of CIS-2-butyl-6-[5-(hydroxymethyl)-2-methyl-3-isoxazolidinyl]-3-[[2'-[1-(triphenylmethyl)-1H-tetrazol-5-yl][1,1'-biphenyl]-4-yl]methyl]-4(3H)-quinazolinone in 100 ml of tetrahydrofuran-methanol containing 2 ml of chloroform is refluxed for 24 hours. The volatiles are evaporated in vacuo to a residue which is dissolved in 1:3 methanol-chloroform and washed with water. The organic layer is dried with anhydrous magnesium sulfate and evaporated to a residue. The residue is purified by chromatography using from 40–90% ethyl acetate in hexanes to give 120 mg of the desired product, m.p. 121° C.

Example 16

TRANS-2-butyl-6-[5-(hydroxymethyl)-2-methyl-3-isoxazolidinyl]-3-[[2'-(1H-tetrazol-5-yl)[1,1'-biphenyl]-4-yl]methyl]-4(3H)-quinazolinone A mixture of 350 mg of TRANS-2-butyl-6-[5-(hydroxymethyl)-2-methyl-3-isoxazolidinyl]-3-[[2'-[1-(triphenylmethyl)-1H-tetrazol-5-yl][1,1'-biphenyl]-4-yl]methyl-4(3H)-quinazolinone in 100 ml of tetrahydrofuran-methanol containing 2 ml of chloroform is refluxed for 24 hours. The volatiles are evaporated in vacuo to a residue which is dissolved in 1:3 methanol-chloroform and washed with water. The organic layer is dried with anhydrous magnesium sulfate and evaporated to a residue. The residue is purified by chromatoggraphy using 9:1 ethyl acetate-hexanes to give 150 mg of the desired product as a yellow solid, m.p. 110° C.

Angiotensin II Antagonists In Vitro Tests Materials and Methods:

Beef adrenals are obtained from a local slaughter house (Maxwell—Cohen). [$^{125}$I](Sar$^1$,Ile$^8$)AngII, S.A. 2200 Ci/mmole, is purchased from Dupont (NEN ®, Boston, Mass.). All unlabeled AngII analogs, Dimethylsulfoxide (DMSO), nucleotides, bovine serum albumin (BSA) are purchased from Sigma Chemical Co., St. Louis, Mo. U.S.A.

Preparation of Membranes:

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2M sucrose. Unless otherwise indicated, all subsequent operations are done at 4° C. The tissue is homogenized in a glass homogenizer with a motor-driven teflon pestle with a clearance of 1.0 mm. The homogenate is centrifuged first at low speed (3,000×g) for 10 min. The resulting pellet is discarded and the supernatant fluid recentrifuged at 10,000×g for 15 minutes to give a $P_2$ pellet. This $P_2$ pellet is discarded and the liquid phase is carefully decanted off in clean centrifuge tubes and recentrifuged at high speed (100,000×g) for 60 min. The translucent final pellet is harvested and combined in a small volume (20–50.0 ml) of 50.0 mM Tris.HCl buffer, pH 7.2. A 100 ul aliquot is withdrawn and the protein content of the preparation is determined by the Lowry's method (Lowry, O. H., Rosebrough, N. F., Farr, A. L. and Randall, R. J., Protein measurement with Folin phenol reagent. J. Biol. Chem , 48, 265–275, 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at −70° C. until use in the binding assays.

Receptor Binding Assay

Binding of [$^{125}$I,Ile$^8$)AngII

The binding of [$^{125}$I](Sar$^1$,Ile$^8$)AngII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I,Ile8)AngII (Specific Activity, 2200 Ci/mmole). Non-specific binding is measured in the presence of 1.0 uM unlabeled (Sar$^1$,Ile$^8$)AngII, added in 20 ul volume. Specific binding for [$^{125}$I](Sar$^1$,Ile$^8$) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [$^{125}$I](Sar$^1$-,Ile$^8$) AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, Md., U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduces the radioactivity retained by the filter blanks. This method is routinely used. The filters are removed from the filter grid and counted in a Parkard ® Cobra Gamma Counter for 1 min. (Packard Instrument Co., Downers Grove, Ill., U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 µM are considered active compounds and are then evaluated in concentration-response experiments to determine their IC$_{50}$ values. The results are shown in Table I.

As can be seen from Table I, the compounds demonstrate excellent Angiotensin II Receptor Binding activity.

The enzyme renin acts on a blood plasma $\alpha_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

The compounds of this invention inhibit the action of AII. By administering a compound of this invention to a rat, and then challenging with angiotensin II, a blockage of the vasopressor response is realized. The results of this test on representative compounds of this invention are shown in Table II.

AII Challenge

Conscious Male Okamoto-Aoki SHR, 16–20 weeks old, weighing approximately 330 g are purchased from Charles River Labs (Wilmington, Mass.). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10–20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to a Statham P23Db pressure transducer, and pulsatile blood pressure is recorded to 10–15 minutes with a Gould Brush recorder. (Chan et al., (Drug Development Res., 18:75–94, 1989).

Angiotensin II (human sequence, Sigma Chem. Co., St. Louis, Mo.) of 0.05 and 0.1 ug/kg i.v. is injected into all rats (predosing response). Then a test compound, vehicle or a known angiotensin II antagonist is administered i.v., i.p. or orally to each set of rats. The two doses of angiotensin II are given to each rat again at 30, 60, 90, 120, 180, 240 and 300 minutes post dosing the compound or vehicle. The vasopressor response of angiotensin II is measured for the increase in systolic blood pressure in mmHg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

TABLE I

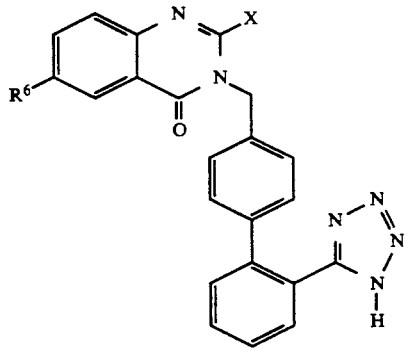

| Ex. No. | R$_6$ | X | Angiotensin II Receptor Binding IC$_{50}$ (M) |
|---|---|---|---|
| 15 | OH, H, O—N—CH$_3$ | —(CH$_2$)$_3$CH$_3$ | 4.3 × 10$^{-8}$ |
| 16 | OH, H, O—N—CH$_3$ | —(CH$_2$)$_3$CH$_3$ | 6.1 × 10$^{-8}$ |

TABLE II

| ANGIOTENSIN II (AII) VASOPRESSOR RESPONSE | | | | | | | | |
|---|---|---|---|---|---|---|---|---|
| | Dose (mg/kg) | AII Dose mcg/kg IV | Min Post Dose | Control Before AII | Response After AII | Change | Average Change | % Inhibition |
| CONTROL | | 0.05 | 0 | 192 | 242 | 50 | 45 | |
| | | | | 200 | 240 | 40 | | |
| | | 0.1 | | 190 | 240 | 50 | 45 | |
| | | | | 200 | 240 | 40 | | |
| Ex. No. | 10 i.v. | 0.05 | 30 | 175 | 180 | 5 | 10 | 78 |

TABLE II-continued

ANGIOTENSIN II (AII) VASOPRESSOR RESPONSE

| | Dose (mg/kg) | AII Dose mcg/kg IV | Min Post Dose | Control Before AII | Response After AII | Change | Average Change | % Inhibition |
|---|---|---|---|---|---|---|---|---|
| 15 | | | | 175 | 190 | 15 | | |
| | 0.1 | | | 185 | 185 | 0 | 0 | 100 |
| | | | | 170 | 170 | 0 | | |
| | 0.05 | | 60 | 190 | 190 | 0 | 0.5 | 99 |
| | | | | 164 | 165 | 1 | | |
| | 0.1 | | | 185 | 193 | 8 | 9 | 80 |
| | | | | 160 | 170 | 10 | | |
| | 0.05 | | 90 | 175 | 180 | 5 | 5 | 89 |
| | | | | 165 | 170 | 5 | | |
| | 0.1 | | | 185 | 195 | 10 | 12.5 | 72 |
| | | | | 160 | 175 | 15 | | |
| | 0.05 | | 120 | 180 | 195 | 15 | 12.5 | 72 |
| | | | | 165 | 175 | 10 | | |
| | 0.1 | | | 175 | 190 | 15 | 12.5 | 72 |
| | | | | 165 | 175 | 10 | | |
| | 0.05 | | 180 | 165 | 195 | 30 | 20 | 56 |
| | | | | 155 | 165 | 10 | | |
| | 0.1 | | | 170 | 205 | 35 | 21.5 | 52 |
| | | | | 157 | 165 | 8 | | |
| | 0.05 | | 240 | 170 | 195 | 25 | 15 | 67 |
| | | | | 155 | 160 | 5 | | |
| | 0.1 | | | 170 | 205 | 35 | 21.5 | 52 |
| | | | | 157 | 165 | 8 | | |
| | 0.05 | | 300 | 168 | 185 | 17 | 13.5 | 70 |
| | | | | 160 | 170 | 10 | | |
| | 0.1 | | | 165 | 190 | 25 | 32.5 | 28 |
| | | | | 160 | 200 | 40 | | |

SPONTANEOUSLY HYPERTENSIVE RATS n = 2 Body weight(s): 320,305 grams

| | Dose (mg/kg) | AII Dose mcg/kg IV | Min Post Dose | Control Before AII | Response After AII | Change | Average Change | % Inhibition |
|---|---|---|---|---|---|---|---|---|
| Control | | 0.05 | 0 | 205 | 255 | 50 | 46 | |
| | | | | 215 | 257 | 42 | | |
| | | 0.1 | | 205 | 255 | 50 | 48.5 | |
| | | | | 210 | 257 | 47 | | |
| Ex. No. 15 | 2.i.v. | 0.05 | 30 | 215 | 237 | 22 | 26 | 43 |
| | | | | 225 | 255 | 30 | | |
| | | 0.1 | | 220 | 245 | 25 | 30 | 38 |
| | | | | 215 | 250 | 35 | | |
| | | 0.05 | 60 | 220 | 245 | 25 | 15 | 67 |
| | | | | 220 | 225 | 5 | | |
| | | 0.1 | | 220 | 255 | 35 | 26.5 | 45 |
| | | | | 217 | 235 | 18 | | |
| | | 0.05 | 90 | 210 | 230 | 20 | 15 | 67 |
| | | | | 225 | 235 | 10 | | |
| | | 0.1 | | 215 | 245 | 30 | 25 | 48 |
| | | | | 220 | 240 | 20 | | |
| | | 0.05 | 120 | 205 | 220 | 15 | 15 | 67 |
| | | | | 215 | 230 | 15 | | |
| | | 0.1 | | 210 | 227 | 17 | 18.5 | 62 |
| | | | | 215 | 235 | 20 | | |
| | | 0.05 | 180 | 203 | 220 | 17 | 26 | 43 |
| | | | | 215 | 250 | 35 | | |
| | | 0.1 | | 210 | 220 | 10 | 22.5 | 54 |
| | | | | 220 | 255 | 35 | | |

SPONTANEOUSLY HYPERTENSIVE RATS n = 2 Body weight(s): 315,345 grams

| | Dose (mg/kg) | AII Dose mcg/kg IV | Min Post Dose | Control Before AII | Response After AII | Change | Average Change | % Inhibition |
|---|---|---|---|---|---|---|---|---|
| Control | | 0.05 | 0 | 210 | 270 | 60 | 52.5 | |
| | | | | 180 | 225 | 45 | | |
| | | 0.1 | | 215 | 270 | 55 | 54 | |
| | | | | 177 | 230 | 53 | | |
| Ex. No. 16 | 10 i.v. | 0.05 | 30 | 195 | 198 | 3 | 8 | 85 |
| | | | | 177 | 190 | 13 | | |
| | | 0.1 | | 190 | 205 | 15 | 10 | 81 |
| | | | | 170 | 175 | 5 | | |
| | | 0.05 | 60 | 195 | 200 | 5 | 12.5 | 76 |
| | | | | 160 | 180 | 20 | | |
| | | 0.1 | | 195 | 210 | 15 | 11.5 | 79 |
| | | | | 165 | 173 | 8 | | |
| | | 0.05 | 90 | 205 | 215 | 10 | 20 | 62 |
| | | | | 160 | 190 | 30 | | |
| | | 0.1 | | 200 | 210 | 10 | 12.5 | 77 |
| | | | | 170 | 185 | 15 | | |
| | | 0.05 | 120 | 195 | 210 | 15 | 17.5 | 67 |
| | | | | 190 | 210 | 20 | | |
| | | 0.1 | | 200 | 220 | 20 | 17.5 | 68 |
| | | | | 185 | 200 | 15 | | |
| | | 0.05 | 180 | 195 | 218 | 23 | 26.5 | 50 |
| | | | | 165 | 195 | 30 | | |

TABLE II-continued
ANGIOTENSIN II (AII) VASOPRESSOR RESPONSE

|      |     |     |     |    |      |    |
|------|-----|-----|-----|----|------|----|
| 0.1  |     | 200 | 215 | 15 | 25   | 54 |
|      |     | 170 | 205 | 35 |      |    |
| 0.05 | 240 | 195 | 218 | 23 | 26.5 | 50 |
|      |     | 165 | 195 | 30 |      |    |
| 0.1  |     | 200 | 215 | 15 | 25   | 54 |
|      |     | 170 | 205 | 35 |      |    |
| 0.05 | 300 | 195 | 230 | 35 | 42.5 | 19 |
|      |     | 175 | 225 | 50 |      |    |
| 0.1  |     | 220 | 250 | 30 | 40   | 26 |
|      |     | 180 | 230 | 50 |      |    |

SPONTANEOUSLY HYPERTENSIVE RATS n = 2 Body weight(s): 300,345 grams

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response, for example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. A quinazolinone compound having the formula:

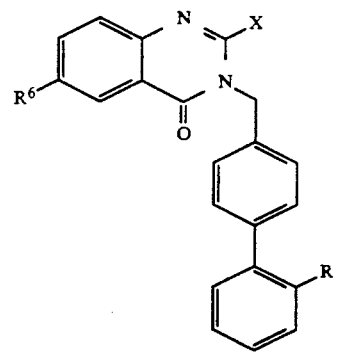

wherein:

R is

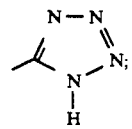

X is straight or branched chain lower alkyl of 3 to 5 carbon atoms;

$R^6$ is

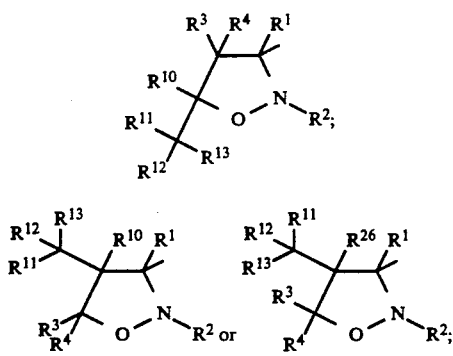

R¹ is H, straight chain lower alkyl of 1 to 4 atoms, —CF₃, —CN, phenyl, substituted phenyl (substitution selected from mono-lower alkyl of 1 to 3 carbon atoms, —CF₃, nitro, O-alkyl of 1 to 3 carbon atoms), pyridine, thiophene or furan;

R² is straight or branched chain lower alkyl of 1 to 4 carbon atoms, cycloalkyl (rings of 3 to 8 carbon atoms), phenyl, substituted phenyl (substitution selected from mono-lower alkyl of 1 to 3 carbon atoms), —CF₃, nitro, O-alkyl of 1 to 3 carbon atoms), pyridine, thiophene, furan, benzyl, substituted benzyl (substitution selected from mono-lower alkyl of 1 to 3 carbon atoms, —CF₃, nitro, O-alkyl of 1 to 3 carbon atoms);

R³ is H, straight or branched lower alky of 1 to 4 carbon atoms, phenyl, substituted phenyl (substitution selected from mono-lower alkyl of 1 to 3 carbon atoms, —CF₃, nitro, O-alkyl of 1 to 3 carbon atoms), pyridine, thiophene, furan, —CHO, —OR¹⁹, —CO₂R¹⁹ or

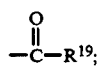

R⁴ is H, straight or branched chain lower alkyl of 1 to 4 carbon atoms, phenyl, substituted phenyl (substitution selected from mono-lower alkyl of 1 to 3 carbon atoms, —CF₃, nitro, O-alkyl of 1 to 3 carbon atoms), pyridine, thiophene, furan, —CHO, —OR¹⁹, —CO₂R¹⁹ or

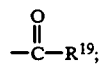

R⁹ is hydrogen, straight chain or branched chain lower alkyl of 1 to 4 carbon atoms;

R¹⁰ is H, straight or branched chain lower alkyl of 1 to 4 carbon atoms, phenyl, substituted phenyl (substitution selected from mono-lower alkyl of 1 to 3 carbon atoms, —CF₃, nitro, O-alkyl of 1 to 3 carbon atoms), pyridine, thiophene, or furan;

R¹¹ is H, straight or branched chain lower alkyl of 1 to 4 carbon atoms, —CF₃, phenyl, substituted phenyl (substitution selected from mono-lower alkyl of 1 to 3 carbon atoms, —CF₃, nitro, O-alkyl of 1 to 3 carbon atoms), pyridine, thiophene, furan, benzyl, subsituted benzyl(substitution selected from mono-lower alkyl of 1 to 3 carbon atoms, —CF₃, nitro, O-alkyl of 1 to 3 carbon atoms), —OR⁹, O-phenyl, O-substituted phenyl(substitution selected from mono-lower alkyl of 1 to 3 carbon atoms, —CF₃, nitro, O-alkyl of 1 to 3 carbon atoms), O-pyridine, O-thiophene, O-furan, —NH₂, —NHR¹⁹, —NR¹⁹R¹⁹, —CO₂R¹⁹, or —CONR⁹R⁹;

R¹² is H, straight or branched chain lower alkyl of 1 to 4 carbon atoms, —CF₃, phenyl, substituted phenyl (substitution selected from mono-lower alkyl of 1 to 3 carbon atoms, —CF₃, nitro, O-alkyl of 1 to 3 carbon atoms), pyridine, thiophene, furan, benzyl, substituted benzyl(substitution selected from mono-lower alkyl of 1 to 3 carbon atoms, —CF₃, nitro, O-alkyl of 1 to 3 carbon atoms), —OR⁹, O-phenyl, O-substituted phenyl(substitution selected from mono lower alkyl of 1 to 3 carbon atoms, —CF₃, nitro, O-alkyl of 1 to 3 carbon atoms), O-pyridine, O-thiophene, O-furan, —NH₂, —NHR¹⁹, —NR¹⁹R¹⁹, —CO₂R¹⁹, or —CONR⁹R⁹;

R¹³ is H, straight or branched chain lower alkyl of 1 to 4 carbon atoms, —CF₃, phenyl, substituted phenyl(substitution selected from mono-lower alkyl of 1 to 3 carbon atoms, —CF₃, nitro, O-alkyl of 1 to 3 carbon atoms), pyridine, thiophene, furan, benzyl, substituted benzyl(substitution selected from mono-lower alkyl of 1 to 3 carbon atoms, —CF₃, nitro, O-alkyl of 1 to 3 carbon atoms), —OR⁹, O-phenyl, O-substituted phenyl(substitution selected from mono-lower alkyl of 1 to 3 carbon atoms, —CF₃, nitro, O-alkyl of 1 to 3 carbon atoms), O-pyridine, O-thiophene, O-furan, —NH₂, —NHR¹⁹, —NR¹⁹R¹⁹, —CO₂R¹⁹, or —CONR⁹R⁹;

R¹⁹ is straight or branched chain lower alkyl of 1 to 4 carbon atoms;

R²⁶ is —CHO, —OR¹⁹, —CO₂R¹⁹ or

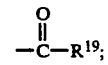

and pharmaceutically acceptable salts thereof.

2. The compound according to claim 1 where in said salts are selected from potassium, sodium, calcium, magnesium or ammonium.

3. The compound according to claim 1 wherein X is a straight chain alkyl of 3 or 4 carbon atoms; R⁶ is

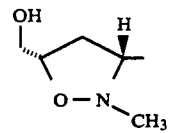

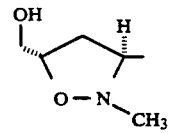

4. The quinazolinone compound of claim 1, wherein:
R¹ is H, straight chain lower alkyl of 1 to 4 carbon atoms;
R² is straight or branched chain lower alkyl of 1 to 4 carbon atoms;
R³ is H, straight or branched chain lower alkyl of 1 to 4 carbon atoms;
R⁴ is H, straight or branched chain lower alkyl of 1 to 4 carbon atoms, $R^9$ is hydrogen, straight or branched chain lower alkyl of 1 to 4 carbon atoms, $R^{10}$ is H, straight or branched chain lower alkyl of 1 to 4 carbon atoms, $R^{11}$ is H straight or branched chain lower alkyl of 1 to 4 carbon atoms, —$OR^9$;

$R^{12}$ is H, straight or branched chain lower alkyl of 1 to 4 carbon atoms, —$OR^9$;

$R^{13}$ is H, straight or branched chain lower alkyl of 1 to 4 carbon atoms, —$OR^9$;

$R^{26}$ is —CHO or —$OR^{19}$.

5. The compound according to claim 4 wherein $R^9$ is H.

6. A quinazolinone compound having the formula:

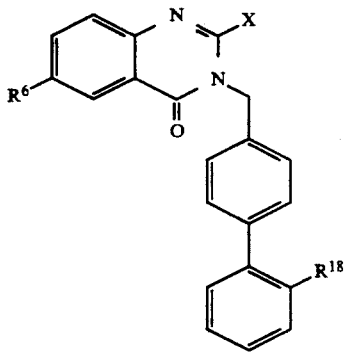

wherein:

X is straight or branched chain alkyl of 3 to 5 carbon atoms;

$R^{18}$ is —CN or

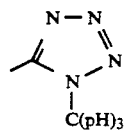

$R^6$ is

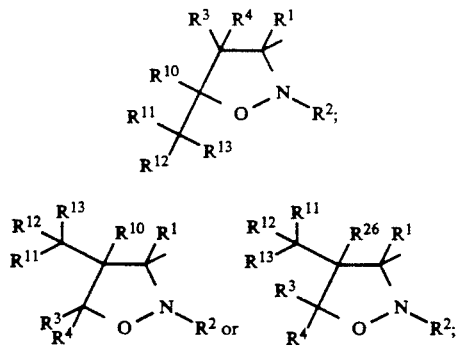

$R^1$ is H, straight chain lower alkyl of 1 to 4 carbon atoms, —$CF_3$, —CN,
phenyl, substituted phenyl (substitution selection from mono-lower alkyl of 1 to 3 carbon atoms, —$CF_3$, nitro, O-alkyl of 1 to 3 carbon atoms), pyridine, thiophene or furan;

$R^2$ is straight or branched chain lower alkyl of 1 to 4 carbon atoms, cycloalkyl (rings of 3 to 8 carbon atoms), phenyl, substituted phenyl (substitution selected from mono-lower alkyl of 1 to 3 carbon atoms, —$CF_3$, nitro, O-alkyl of 1 to 3 carbon atoms), pyridine, thiophene, furan, benzyl, substituted benzyl(substitution selected from mono-lower alkyl of 1 to 3 carbon atoms, —$CF_3$, nitro, O-alkyl of 1 to 3 carbon atoms);

$R^3$ is H, straight or branched chain lower alkyl of 1 to 4 carbon atoms, phenyl, substituted phenyl(substitution selected from mono-lower alkyl of 1 to 3 carbon atoms, —$CF_3$, nitro, O-alkyl of 1 to 3 carbon atoms), pyridine, thiophene, or furan; —CHO, —$CO_2R^{19}$ or

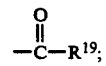

$R^4$ is H, straight or branched chain lower alkyl of 1 to 4 carbon atoms, phenyl, substituted phenyl(substitution selected from mono-lower alkyl of 1 to 3 carbon atoms, —$CF_3$, nitro, O-alkyl of 1 to 3 carbon atoms), pyridine, thiophene, furan, —CHO, —$OR^{19}$, —$CO_2R^{19}$ or

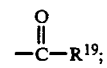

$R^9$ is hydrogen, straight or branched chain lower alkyl of 1 to 4 carbon atoms;

$R^{10}$ is H, straight or branched chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms), pyridine, thiophene, or furan;

$R^{11}$ is H, straight or branched chain lower alkyl of 1 to 4 carbon atoms, —$CF_3$, phenyl, substituted phenyl (substitution selected from mono-lower alkyl of 1 to 3 carbon atoms, —$CF_3$, nitro, O-alkyl of 1 to 3 carbon atoms), pyridine, thiophene, furan, benzyl, subsituted benzyl(substitution selected from mono-lower alkyl of 1 to 3 carbon atoms, —$CF_3$, nitro, O-alkyl of 1 to 3 carbon atoms), —$OR^9$, O-phenyl, O-substituted phenyl (substitution selected from mono-lower alkyl of 1 to 3 carbon atoms, —$CF_3$, nitro, O-alkyl of 1 to 3 carbon atoms), O-pyridine, O-thiophene, O-furan, —$NH_2$, —$NHR^{19}$, —$NR^{19}R^{19}$, —$CO_2R^{19}$, or —$CONR^9R^9$;

$R^{12}$ is H, straight or branched chain lower alkyl of 1 to 4 carbon atoms, —$CF_3$, phenyl, substituted phenyl(substitution selected from mono-lower alkyl of 1 to 3 carbon atoms —$CF_3$, nitro, O-alkyl of 1 to 3 carbon atoms), pyridine, thiophene, furan, benzyl, substituted benzyl(substitution selected from mono-lower alkyl of 1 to 3 carbon atoms, —$CF_3$, nitro, O-alkyl of 1 to 3 carbon atoms), —$OR^9$, O-phenyl, O-substituted phenyl(substitution selected from mono lower alkyl of 1 to 3 carbon atoms, —$CF_3$, nitro, O-alkyl of 1 to 3 carbon atoms), O-pyridine, O-thiophene, O-furan, —$NH_2$, —$NHR^{19}$, —$NR^{19}R^{19}$, —$CO_2R^{19}$, or —$CONR^9R^9$;

$R^{13}$ is H, straight or branched chain lower alkyl of 1 to 4 carbon atoms, —$CF_3$, phenyl, substituted phenyl(substitution selected from mono-lower alkyl of 1 to 3 carbon atoms, —$CF_3$, nitro, O-alkyl of 1 to 3 carbon atoms), pyridine, thiophene, furan, benzyl, substituted benzyl(substitution selected from mono-lower alkyl of 1 to 3 carbon atoms, —$CF_3$, nitro, O-alkyl of 1 to 3 carbon atoms), —$OR^9$, O-phenyl, O-substituted phenyl(substitution selected from mono-lower alkyl of 1 to 3 carbon atoms, —CF₃, nitro, O-alkyl of 1 to 3 carbon atoms), O-pyridine, O-thiophene, O-furan, —NH₂, —NHR¹⁹, —NR¹⁹R¹⁹, —CO₂R¹⁹, or —CONR⁹R⁹;

R¹⁹ is straight or branched chain lower alkyl of 1 to 4 carbon atoms;

R²⁶ is —CHO, —OR¹⁹, —CO₂R¹⁹ or

7. The compound according to claim 6 wherein X is a straight chain alkyl of 3 or 4 carbon atoms; R⁶ is

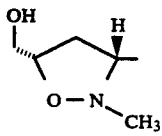

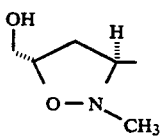

8. The compound according to claim 1, CIS-2-butyl-6-[5-(hydroxymethyl)-2-methyl-3-isoxazolidinyl]-3-[[2'-(1H-tetrazol-5-yl)[1,1'-biphenyl]-4-yl]methyl]-4(3H)-quinazolinone.

9. The compound according to claim 1, trans-2-butyl-6-[5-(hydroxymethyl-2-methyl-3-isoxazolidinyl]-3-[[2'-(1H-tetrazol-5-yl)[1,1'-biphenyl]-4-yl]methyl]-4(3H)-quinazolinone.

10. The compound according to claim 6, cis-2-butyl-6-[5-(hydroxymethyl)-2-methyl-3-isoxazolidinyl]-3-[[2'-cyano[1,1'-biphenyl]-4-yl]-methyl]-4(3H)-quinazolinone.

11. The compound according to claim 6, trans-2-butyl-6-[5-(hydroxymethyl)-2-methyl-3-isoxazolidinyl]-3-[[2'-cyano[1,1'-biphenyl]-4-yl]-methyl]-4(3H)-quinazolinone.

12. The compound according to claim 6, cis-2-butyl-6-[5-(hydroxymethyl)-2-methyl-3-isoxazolidinyl]-3-[[2'-[1-(triphenylmethyl)-1H-tetrazol-5-yl-1][1,1'-biphenyl]-4-yl]methyl]-4(3H)-quinazolinone.

13. The compound according to claim 6, trans-2-butyl-6-[5-(hydroxymethyl)-2-methyl-3-isoxazolidinyl)-3-[[2'-[1-(triphenylmethyl)-1H-tetrazol-5-yl][1,1'-biphenyl]-4-yl]methyl]-4(3H)quinazolinone.

14. A quinazolinone compound having the formula.

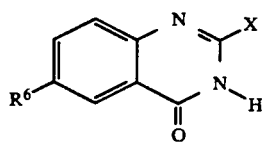

X is straight or branched chain lower alkyl of 3 to 5 carbon atoms; R⁶ is

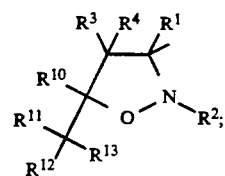

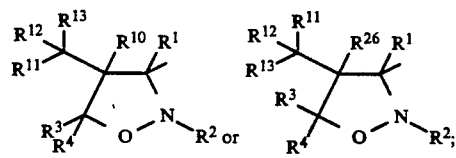

R¹ is H, straight chain lower alkyl of 1 to 4 carbon atoms, —CF₃, —CN, phenyl, substituted phenyl (substitution selection from mono-lower alkyl of 1 to 3 carbon atoms, —CF₃, nitro, O-alkyl of 1 to 3 carbon atoms), pyridine, thiophene or furan;

R² is straight or branched chain lower alkyl of 1 to 4 carbon atoms, cycloalkyl (rings of 3 to 8 carbon atoms), phenyl, substituted phenyl (substitution selected from mono-lower alkyl of 1 to 3 carbon atoms, —CF₃, nitro, O-alkyl of 1 to 3 carbon atoms), pyridine, thiophene, furan, benzyl, substituted benzyl(substitution selected from mono-lower alkyl of 1 to 3 carbon atoms, —CF₃, nitro, O-alkyl of 1 to 3 carbon atoms);

R³ is H, straight or branched chain lower alkyl of 1 to 4 carbon atoms, phenyl, substituted phenyl(substitution selected from mono-lower alkyl of 1 to 3 carbon atoms, —CF₃, nitro, O-alkyl of 1 to 3 carbon atoms), pyridine, thiophene, or furan; —CHO, —OR¹⁹, —CO₂R¹⁹ or

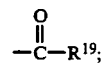

R⁴ is H, straight or branched chain lower alkyl of 1 to 4 carbon atoms, phenyl, substituted phenyl(substitution selected from mono-lower alkyl of 1 to 3 carbon atoms, —CF₃, nitro, O-alkyl of 1 to 3 carbon atoms), pyridine, thiophene, furan, —CHO, —OR¹⁹, —CO₂R¹⁹ or

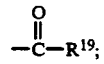

R⁹ is hydrogen, straight or branched chain lower alkyl of 1 to 4 carbon atoms;

R¹⁰ is H, straight or branched chain lower alkyl of 1 to 4 carbon atoms, phenyl, substituted phenyl (substitution selected from mono-lower alkyl of 1 to 3 carbon atoms, —CF₃, nitro, O-alkyl of 1 to 3 carbon atoms), pyridine, thiophene, or furan;

R¹¹ is H, straight or branched chain lower alkyl of 1 to 4 carbon atoms, —CF₃, phenyl, substituted phenyl (substitution selected from mono-lower alkyl of 1 to 3 carbon atoms, —CF₃, nitro, O-alkyl of 1 to 3 carbon atoms), pyridine, thiophene, furan, benzyl, subsituted benzyl(substitution selected from mono-lower alkyl of 1 to 3 carbon atoms, —CF₃, nitro, O-alkyl of 1 to 3 carbon atoms), —OR⁹, O-phenyl, O-substituted phenyl(substitution selected from mono-lower alkyl of 1 to 3 carbon atoms, —CF$_3$, nitro, O-alkyl of 1 to 3 carbon atoms), O-pyridine, O-thiophene, O-furan, —NH$_2$, —NHR$^{19}$, —NR$^{19}$R$^{19}$, —CO$_2$R$^{19}$, or —CONR$^9$R$^9$;

R$^{12}$ is H, straight or branched chain lower alkyl of 1 to 4 carbon atoms, —CF$_3$, phenyl, substituted phenyl(-substitution selected from mono-lower alkyl of 1 to 3 carbon atoms —CF$_3$, nitro, O-alkyl of 1 to 3 carbon atoms), pyridine, thiophene, furan, benzyl, substituted benzyl(substitution selected from mono-lower alkyl of 1 to 3 carbon atoms, —CF$_3$, nitro, O-alkyl of 1 to 3 carbon atoms), —OR$^9$, O-phenyl, O-substituted phenyl(substitution selected from mono lower alkyl of 1 to 3 carbon atoms, —CF$_3$, nitro, O-alkyl of 1 to 3 carbon atoms), O-pyridine, O-thiophene, O-furan, —NH$_2$, —NHR$^{19}$, —NR$^{19}$R$^{19}$, —CO$_2$R$^{19}$, or —CONR$^9$R$^9$;

R$^{13}$ is H, straight or branched chain lower alkyl of 1 to 4 carbon atoms, —CF$_3$, phenyl, substituted phenyl(-substitution selected from mono-lower alkyl of 1 to 3 carbon atoms, —CF$_3$, nitro, O-alkyl of 1 to 3 carbon atoms), pyridine, thiophene, furan, benzyl, substituted benzyl(substitution selected from mono-lower alkyl of 1 to 3 carbon atoms, —CF$_3$, nitro, O-alkyl of 1 to 3 carbon atoms), —OR$^9$, O-phenyl, O-substituted phenyl(substitution selected from mono-lower alkyl of 1 to 3 carbon atoms, —CF$_3$, nitro, O-alkyl of 1 to 3 carbon atoms), O-pyridine, O-thiophene, O-furan, —NH$_2$, —NHR$^{19}$, —NR$^{19}$R$^{19}$, —CO$_2$R$^{19}$, or —CONR$^9$R$^9$;

R$^{19}$ is straight or branched chain lower alkyl of 1 to 4 carbon atoms;

R$^{26}$ is —CHO, —OR$^{19}$, —CO$_2$R$^{19}$ or

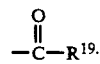

15. The compound according to claim 14, wherein X is a straight chain alkyl of 3 to 4 carbon atoms; R$^6$ is

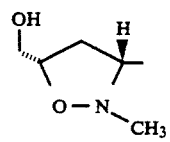

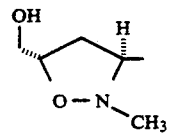

16. The compound according to claim 15, trans-2-butyl-6[5-(hydroxymethyl)-2-methyl-3-isoxazolidinyl]-4(1H)-quinazolinone.

17. The compound according to claim 15, cis-2-butyl-6-[5-(hydroxymethyl)-2-methyl-3-isoxazolidinyl]-4(1H)-quinazolinone.

18. A pharmaceutical composition useful for treating angiotensin produced hypertension or congestive heart failure in a mammal comprising a suitable pharmaceutical carrier and an effective amount of a compound of claim 1.

19. A method of treating angiotensin induced hypertension in a mammal comprising administering a compound of claim 1 to said mammal an amount effective to lower angiotensin induced hypertension.

20. A method of treating congestive heart failure in a mammal comprising administering a compound of claim 1 to said mammal in an amount effective to treat the effects of Angiotensin II.

21. A method of antagonizing the effects of Angiotensin II in a mammal comprising administering a compound of claim 1 to said mammal in an amount effective to treat the effects of Angiotensin II.

* * * * *